United States Patent
Wen et al.

(10) Patent No.: US 12,366,046 B1
(45) Date of Patent: Jul. 22, 2025

(54) PILE FOUNDATION BEARING PERFORMANCE TESTING DEVICE AND METHOD

(71) Applicant: Northwest Institute of Eco-Environment and Resources, Chinese Academy of Sciences, Gansu (CN)

(72) Inventors: Zhi Wen, Gansu (CN); Yasheng Li, Gansu (CN); Fei Wang, Gansu (CN); Qiang Gao, Gansu (CN)

(73) Assignee: Northwest Institute of Eco-Environment and Resources, Chinese Academy of Sciences, Gansu (CN)

( * ) Notice: Subject to any disclaimer, the term of this patent is extended or adjusted under 35 U.S.C. 154(b) by 0 days.

(21) Appl. No.: 19/015,694

(22) Filed: Jan. 10, 2025

(30) Foreign Application Priority Data

Jan. 17, 2024 (CN) .......................... 202410068210.8

(51) Int. Cl.
*E02D 33/00* (2006.01)
*G01N 33/38* (2006.01)

(52) U.S. Cl.
CPC ........... *E02D 33/00* (2013.01); *G01N 33/383* (2013.01)

(58) Field of Classification Search
CPC .............................. E02D 33/00; G01N 33/383
See application file for complete search history.

(56) References Cited

U.S. PATENT DOCUMENTS 2,674,876 A * 4/1954 Caudill ................. G01M 5/005
73/84
4,614,110 A * 9/1986 Osterberg ............... E02D 33/00
73/84
(Continued)

FOREIGN PATENT DOCUMENTS

CN         103061361 A       4/2013
CN         108589808 A       9/2018
(Continued)

OTHER PUBLICATIONS

Yu, Dezhong et al., "Experimental Study on the Pile Side Friction Resistance of the Island Permafrost Bridge Pile Foundation after Freezing and Thawing", Journal of China & Foreign Highway, vol. 35, No. 6, pp. 105-109, Dec. 31, 2015.

*Primary Examiner* — Laura Martin
*Assistant Examiner* — Philip L Cotey
(74) *Attorney, Agent, or Firm* — CKC & Partners Co., LLC

(57) ABSTRACT

A pile foundation bearing performance testing device and method are disclosed. The main body of the present invention is a pile body provided with a hydraulic jack at the bottom, and in the end-bearing friction pile test, the pile foundation service performance test can be conducted under different proportion conditions of the pile side resistance and the pile tip resistance of the pile foundation, and concrete is poured onto the surface of the pile body of the pile foundation bearing performance testing device to form a precast pile and then the pile is driven in permafrost to realize the load service performance test of the precast pile in the permafrost area, and the pile foundation bearing performance testing device is placed into a drilled hole and concrete is poured around the pile to realize the pile foundation service performance test of a bored cast-in-place pile.

6 Claims, 4 Drawing Sheets

(56) References Cited

U.S. PATENT DOCUMENTS

| | | | | |
|---|---|---|---|---|
| 4,715,726 | A * | 12/1987 | Tsuruta | G01N 33/383 |
| | | | | 374/53 |
| 5,576,494 | A * | 11/1996 | Osterberg | E02D 1/022 |
| | | | | 73/803 |
| 8,596,136 | B2 * | 12/2013 | Hecht | E02D 33/00 |
| | | | | 73/803 |
| 9,499,956 | B2 * | 11/2016 | Hayes | G01M 99/007 |
| 9,977,008 | B2 * | 5/2018 | England | G01K 13/10 |
| 10,472,793 | B2 * | 11/2019 | Bell | E21B 47/135 |
| 11,060,947 | B2 * | 7/2021 | Moghaddam | G01M 5/0058 |
| 2001/0035053 | A1 * | 11/2001 | McAfee | B28B 7/0094 |
| | | | | 73/803 |
| 2006/0021446 | A1 * | 2/2006 | England | E02D 33/00 |
| | | | | 73/784 |
| 2011/0200068 | A1 * | 8/2011 | Piscsalko | G01K 13/10 |
| | | | | 374/152 |
| 2016/0251819 | A1 * | 9/2016 | Dinh | E02D 33/00 |
| | | | | 73/784 |
| 2020/0102826 | A1 * | 4/2020 | Sun | E21D 21/0033 |
| 2021/0172926 | A1 * | 6/2021 | England | E02D 33/00 |
| 2023/0251166 | A1 * | 8/2023 | Li | G01M 13/025 |
| | | | | 73/865.9 |

FOREIGN PATENT DOCUMENTS

| | | | |
|---|---|---|---|
| CN | 108951724 | A | 12/2018 |
| CN | 109653259 | A | 4/2019 |
| CN | 217267699 | U | 8/2022 |
| CN | 115419042 | A | 12/2022 |
| JP | H01116424 | A | 5/1989 |
| JP | H02178416 | A | 7/1990 |

\* cited by examiner

PILE FOUNDATION BEARING PERFORMANCE TESTING DEVICE AND METHOD

CROSS-REFERENCE TO RELATED APPLICATIONS

This non-provisional application claims priority under 35 U.S.C. § 119 (a) to patent application Ser. No. 202410068210.8 filed in P.R. China on Jan. 17, 2024, the entire contents of which are hereby incorporated by reference.

Some references, if any, which may include patents, patent applications and various publications, may be cited and discussed in the description of this application. The citation and/or discussion of such references, if any, is provided merely to clarify the description of this application and is not an admission that any such reference is "prior art" to the application described herein. All references listed, cited and/or discussed in this specification are incorporated herein by reference in their entirety and to the same extent as if each reference was individually incorporated by reference.

FIELD OF THE INVENTION

The present invention belongs to the field of pile foundation testing devices and methods, in particular to a pile foundation bearing performance testing device and method.

BACKGROUND OF THE INVENTION

With the continuous development of China's economy, the demand for engineering and construction is becoming increasingly strong in the high-latitude permafrost area of the Tibetan Plateau and the high-latitude permafrost area in northeast China; in the construction of the subgrade, the construction of various bridges, such as land bridges, cannot be separated from the design and application of the pile foundation; to avoid the destruction of the buildings and structures in the permafrost areas, such as houses, during the freezing and thawing process of the active layer, pile foundation scheme used in deep foundation is often adopted. According to the role played by the pile foundation in engineering buildings and structures, the pile foundation can be divided into uplift piles and compression piles; the pile foundation bearing capacity of compression piles depends mainly on the pile side resistance and pile tip resistance, and it is also divided into end-bearing piles, end-bearing friction piles, and friction piles according to the supporting part of the main bearing capacity of pile foundation. All the piles are applied in permafrost areas. Since the pile tips of end-bearing piles usually penetrate deep into the non-frozen bedrock below the permafrost layer or the bearing stratum which can be used as the bedrock, the pile body will inevitably contact with the frozen soil layer and freeze when it passes through the frozen soil layer, so that the end-bearing piles take on the role of end-bearing friction piles. Similar to the friction piles in compression piles, the pile foundation service performance of an uplift pile depends mainly on the pile side resistance. In the permafrost area, the main factor affecting the pile side resistance in the frozen state is the freezing force between the pile body and the frozen soil. Regardless of whether is in the frozen or thawn state, the force between the pile body and the soil around the pile can be called the frictional resistance of the pile side. The main factors affecting the freezing force at the pile-soil interface are temperature, soil moisture content, and the frictional resistance between the pile body concrete and soil particles; the main factors affecting the frictional resistance of the pile side between the pile and the soil surrounding the pile in the thawed state are the moisture content of the soil surrounding the pile, and the frictional resistance between the pile and soil particles. As the global temperature is increasing year by year and the permafrost temperature fluctuates in the inter-annual range in the project area where the pile foundation is located, the frictional resistance of the pile side between the pile body and the soil around the pile is fluctuating, which makes the pile side resistance change, and in this case, the pile tip resistance of the end-bearing friction pile fluctuates accordingly. It is not known whether the fluctuation of the proportion of the pile side resistance and pile tip resistance of end-bearing friction piles and the fluctuation of the pile side resistance of the friction piles have an impact on the pile foundation service performance, and no standardized test method is available to testing for the time being.

At present, in engineering construction, the single pile load test is commonly used for in-situ service performance test of pile foundation; in the compression pile foundation bearing performance test, cement blocks are always arranged on top of the pile as the upper load, and in the uplift pile service performance test, a reaction frame is often arranged on the ground to apply a force of pull up to the pile body for the pile foundation bearing performance test; there are disadvantages of not easy to dismantle the existing test piles and high cost of the test piles after completion of the test. As the ground temperature in the permafrost area is fluctuating and the soil temperature around the pile is slowly rising in the context of global warming, the existing in-situ pile testing method is unable to test the pile side resistance after a change in the temperature of soil around the pile; in the end-bearing friction pile test of compression piles, the existing method for testing pile foundation bearing performance cannot test the pile foundation service performance under the different proportion conditions of the pile side resistance and the pile tip resistance.

To this end, the present invention provides a reusable pile foundation service performance testing device that can be used for testing pile foundation bearing performance in permafrost areas at different ground temperatures. The main body of the present invention is a pile body provided with a hydraulic jack at the bottom, and in the end-bearing friction pile test, the pile foundation service performance test is conducted under different conditions of the pile side resistance and the pile tip resistance by applying the upper dead load to the top of the pile body and applying the load at the bottom of the pile by means of the hydraulic jack; by enabling the hydraulic jack at the bottom of the present invention to drive the piston lever head to detach from the contact with the soil at the pile tip, the end-bearing friction pile can become the friction pile, and the present invention can carry out the pile foundation bearing performance test of a pressure-bearing friction pile; by enabling the hydraulic jack at the bottom of the present invention to drive the piston lever head to contact the soil at the pile tip, so that the pile body undergoes upward movement relative to the soil around the pile, the uplift pile service performance test can be conducted; the temperature of soil around the pile is controlled by enabling the cold bath machine to inject an antifreezing solution into the liquid-cooling chamber inside the pile body and circulate it, and combined with different methods for applying loads to the pile foundation, the pile foundation service performance tests of pressure-bearing end-bearing friction piles, pressure-bearing friction piles and uplift piles can be realized at different ground temperatures. Compared with the previous cast-in-place test piles, the present invention can test the pile foundation bearing performance at different ground temperatures; the present invention can study the deterioration in the pile foundation service performance caused by changes in the proportion of the pile side resistance and the pile tip resistance due to fluctuations in ground temperatures; the present invention can artificially change the proportion of the pile side resistance and the pile tip resistance by arranging the hydraulic jack at the bottom of the pile foundation and applying a dead load on the top of the pile with concrete blocks and can be used to test the pile foundation service performance of pressure-bearing end-bearing friction piles, pressure-bearing friction piles, uplift piles, etc.; concrete is poured onto the surface of the pile body in the present invention to form a precast pile, and the precast pile is driven into permafrost to realize the load service performance test of the precast pile in the permafrost area; the present invention is placed in a drilled hole and concrete is poured around a pile to realize the pile foundation service performance test of a bored cast-in-place pile; in addition to being used in the permafrost areas, the present invention can also be used in non-permafrost areas, with the same application prospects as those in the permafrost areas; the present invention has the advantage of a low level of difficulty in reuse difficulty, and the permafrost around the pile can thaw by enabling the cold bath machine to inject a high-temperature antifreezing solution into the pile body, and after the freezing force between the pile and permafrost disappears, a crane can be used to remove the present invention from the pile hole for reuse.

SUMMARY OF THE INVENTION

The technical problem to be solved by the present invention is: for the defect that the prior art is unable to test and study the pile foundation service performance under the different proportion conditions of the pile side resistance and the pile tip resistance, the present invention is to solve the technical problem of how to realize the test of the pile foundation service performance under the different proportion conditions of the pile side resistance and the pile tip resistance between the pile foundations of the cast-in-place pile and the precast pile.

The technical solution of the present invention is as follows:

A pile foundation bearing performance testing device includes a pile body, a hydraulic jack is provided inside a pile bottom of the pile body, and a piston lever head of the hydraulic jack is oriented downward, an earth pressure cell is provided on the piston lever head of the hydraulic jack, a pointed boot is provided at a bottom of the earth pressure cell, and a ring is provided at a lower part of the pile body.

In a further technical solution, an interlayer is disposed in a side wall of the pile body to form a liquid-cooling chamber, a cold bath pipe is provided inside the liquid-cooling chamber, a liquid outlet is configured on an outer wall of the pile body located at an upper end of the liquid-cooling chamber, and the cold bath pipe has a main body including a vertical steel pipe and a ring steel pipe with a hole and disposed at the bottom of the liquid-cooling chamber.

In a further technical solution, a water displacement gauge bracket is provided at a side of a top of the pile body for installation of a water displacement gauge tube No. 1, and a reference point bracket is provided at a position which is spaced apart from the test pile by a certain distance and experiences no ground settlement during the test to install a water displacement gauge tube No. 2 thereon, and the water displace gauge tube No. 1 and the water displacement gauge tube No. 2 are connected through a low-temperature resistant water pipe.

A method for testing pile foundation bearing performance applied to a pile foundation bearing performance testing device, including a cast-in-place pile foundation bearing performance test in the following steps:

step A1, drilling a hole in a target test area to form a drilled hole, installing the ring on a bottom end of the pile body, then placing the pile foundation bearing performance testing device into the drilled hole, pressurizing the hydraulic jack with a hydraulic machine so that the earth pressure cell on the piston lever head is in contact with a soil body at a bottom of the drilled hole, pouring concrete into a gap between the pile body and the drilled hole, and curing the concrete;

step A2, pressurizing the hydraulic jack with the hydraulic machine so that the piston lever head is accommodated into the hydraulic jack, at that time, applying a load to a top of the pile body is a pile foundation bearing performance test of a friction pile;

step A3, making the earth pressure cell on the piston lever head in full contact with the soil body and the earth pressure cell show a pressure borne by a soil body at a pile tip, applying a load greater than the value of the pressure borne by the soil body at the pile tip shown by the earth pressure cell to the top of the pile body is a service performance test of an end-bearing friction pile;

step A4, applying no load to the top of the pile body, and enabling the hydraulic jack to drive the piston lever head so that the earth pressure cell or the pointed boot is in full contact with the soil body is a service performance test of an uplift pile;

step A5, adjusting a pile side resistance and a pile tip resistance of the end-bearing friction pile, applying various overlying dead loads to the top of the pile body, and adjusting the load values applied to the pile body and the soil body at the bottom of the drilled hole by the hydraulic jack at the bottom of the pile body to change the pile side resistance and the pile tip resistance as well as proportions thereof, where for the pile body, the difference between a load applied to the top of the pile body and the load applied by the hydraulic jack is a value of the pile side resistance, and the value of the load applied by the hydraulic jack to the soil body at the bottom of the drilled hole is a value of the pile tip resistance; and step A6, upon completion of the test, pulling the pile foundation bearing performance testing device attached with concrete out of the drilled hole using a crane, and removing the concrete on the surface of the pile body by means of a concrete breaking hammer for next use of the pile foundation bearing performance testing device.

In a further technical solution, a displacement of the pile body during the bearing performance test of the end-bearing friction pile is jointly measured by means of the water displacement gauge tube No. 1 installed on the top of the pile body and the water displacement gauge tube No. 2 installed on the ground; and an electromagnetic displacement transducer is additionally secured at the position of the piston lever head of the hydraulic jack for displacement monitoring, thus the difference between a pile top displacement and a pile bottom displacement is used to calculate a pile body displacement and a pile tip displacement of the end-bearing friction pile under different proportion conditions of the pile side resistance and the pile tip resistance.

In a further technical solution, during the test process, a cold bath machine is used to adjust a temperature of an antifreezing solution entering the liquid-cooling chamber of the pile body to a target testing temperature, the pile foundation bearing performance is successively tested under different temperature conditions, and the cold bath machine is adjusted to raise the temperature of the antifreezing solution entering the liquid-cooling chamber of the pile body to a positive temperature after completion of the test, so as to thaw frozen soil around the pile body, and the hydraulic jack is pressurized by means of the hydraulic machine to make the piston lever head pressurize the soil body at the bottom of the drilled hole, so that the pile body and the thawed soil are released from the frozen state.

A method for testing pile foundation bearing performance applied to a pile foundation bearing performance testing device, including a precast pile foundation bearing performance test in the following steps:

step B1: accommodating the piston lever head into the hydraulic jack, installing the pointed boot onto the outside of the earth pressure cell of the piston lever head, and removing the ring if it is installed at the bottom of the pile body;

step B2, placing the pile foundation bearing performance testing device into the precast pile mold, pouring concrete in the gap between the pile body and the precast pile mold, and removing the precast pile mold after curing until the concrete reaches strength to form a precast pile;

step B3, using pile pressing equipment to press the precast pile into a soil layer;

step B4, pressurizing the hydraulic jack with the hydraulic machine so that the piston lever head is accommodated into the hydraulic jack, at that time, applying a load to a top of the pile body is a pile foundation bearing performance test of a friction pile;

step B5, making the pointed boot on the piston lever head in full contact with the soil body and the earth pressure cell show a pressure borne by a soil body at a pile tip, applying a load greater than the value of the pressure borne by the soil body at the pile tip shown by the earth pressure cell to the top of the pile body is a service performance test of an end-bearing friction pile;

step B6, applying no load to the top of the pile body, and enabling the hydraulic jack to drive the piston lever head so that the pointed boot is in full contact with the soil body is a service performance test of an uplift pile;

step B7, adjusting a pile side resistance and a pile tip resistance of the end-bearing friction pile, applying various overlying dead loads to the top of the pile body, and adjusting the load values applied to the pile body and the soil body of the soil layer by the hydraulic jack at the bottom of the pile body to change the pile side resistance and the pile tip resistance as well as proportions thereof, where for the pile body, the difference between a load applied to the top of the pile body and the load applied by the hydraulic jack is a value of the pile side resistance, and the value of the load applied by the hydraulic jack to the soil body of the soil layer is a value of the pile tip resistance; and step B8, upon completion of the test, pulling the pile foundation bearing performance testing device attached with concrete out of the soil layer using a crane, and removing the concrete on the surface of the pile body by means of a concrete breaking hammer for next use of the pile foundation bearing performance testing device.

In a further technical solution, a displacement of the pile body during the bearing performance test of the end-bearing friction pile is jointly measured by means of the water displacement gauge tube No. 1 installed on the top of the pile body and the water displacement gauge tube No. 2 installed on the ground; and an electromagnetic displacement transducer is additionally secured at the position of the piston lever head of the hydraulic jack for displacement monitoring, thus the difference between a pile top displacement and a pile bottom displacement is used to calculate a pile body displacement and a pile tip displacement of the end-bearing friction pile under different proportion conditions of the pile side resistance and the pile tip resistance.

In a further technical solution, during the test process, a cold bath machine is used to adjust a temperature of an antifreezing solution entering the liquid-cooling chamber of the pile body to a target testing temperature, the pile foundation bearing performance is successively tested under different temperature conditions, and the cold bath machine is adjusted to raise the temperature of the antifreezing solution entering the liquid-cooling chamber of the pile body to a positive temperature after completion of the test, so as to thaw frozen soil around the pile body, and the hydraulic jack is pressurized by means of the hydraulic machine to make the piston lever head pressurize the soil body at the bottom of the drilled hole, so that the pile body and the thawing soil are released from the frozen state.

To sum up, after the above technical solution is used, the beneficial effects of the present invention are as follows:

(1) By disposing an interlayer inside a side wall of the pile body to form a liquid-cooling chamber, providing a cold bath pipe inside the liquid-cooling chamber, configuring a liquid outlet on an outer wall of the pile body located at an upper end of the liquid-cooling chamber, and providing the cold bath pipe with a main body comprising a vertical steel pipe and a ring steel pipe with a hole and disposed at the bottom of the liquid-cooling chamber, the cold bath system formed by connecting the cold bath pipe and the liquid outlet with the cold bath machine can control the temperature of the frozen soil layer on the side of the pile to test the pile foundation bearing performance at different ground temperatures; compared with the previous test previous cast-in-place test piles, the present invention can test the pile foundation bearing performance at different ground temperatures.

(2) The main body of the present invention is a pile body provided with a hydraulic jack at the bottom, and in the end-bearing friction pile test, the pile foundation service performance can be tested under different conditions of the pile side resistance and the pile tip resistance with the collaboration between the dead load at the top of the pile body and the hydraulic jack arranged at the bottom of the pile; the present invention can study the deterioration in the pile foundation service performance under different proportion conditions of the pile side resistance and the pile tip resistance and at different ground temperatures, so as to realize the pile foundation service performance test under different proportion conditions of the pile side resistance and the pile tip resistance of a pile foundation.

(3) By enabling the hydraulic jack at the bottom of the pile foundation bearing performance testing device to drive the piston lever head to detach from the contact with the soil at the pile tip, the end-bearing friction pile can become the friction pile, and the present invention can carry out the pile foundation bearing performance test of a pressure-bearing friction pile; by enabling the hydraulic jack at the bottom of the pile foundation bearing performance testing device to drive the piston lever head to contact the soil at the pile tip, without applying an upper dead load to the top of the pile body, so that the pile body undergoes upward movement relative to the soil around the pile, the uplift pile service performance test can be conducted.

(4) The present invention can be applied to the pile foundation bearing performance test of bored cast-in-place piles and precast piles, wherein concrete is poured onto the surface of the pile body of the pile foundation bearing performance testing device to form a precast pile and the precast pile is driven into permafrost to realize the load service performance test of the precast pile in the permafrost area, and the pile foundation bearing performance testing device is placed in a drilled hole and concrete is poured around a pile to realize the pile foundation service performance test of a bored cast-in-place pile.

(5) The present invention has the advantages of easy pull-out and repeated use; when the present invention is used in the permafrost area, the permafrost around the pile body can thaw by using the cold bath machine to inject a high-temperature antifreezing solution into the pile body, and after the freezing force between the pile and permafrost disappears, the contact surface between the pile foundation and the soil on the pile side breaks up under the jacking action of the hydraulic jack arranged at the bottom of pile body, and the present invention can be easily pulled out of a pile hole with the help of lifting equipment; in the non-permafrost area, the present invention can be easily pulled out of a pile hole with the upward force exerted on the pile body through the hydraulic jack arranged at the bottom of the pile body and with the help of lifting equipment at the top of the pile body; after it is pulled out and concrete is removed from its surface by knocking, the pile body can be reused many times.

(6) The present invention is applicable to a wide range of pile foundation service performance tests; the present invention can be used for the service performance test of pressure-bearing end-bearing friction piles, pressure-bearing friction piles, and uplift piles and can also be used in both the non-permafrost area and the non-permafrost area.

DETAILED DESCRIPTION OF THE EXEMPLARY EMBODIMENT

The present invention will be further described in detail in combination with drawings and embodiments for clear understanding of the purpose, technical solutions and advantages of the present invention.

Figure 1:
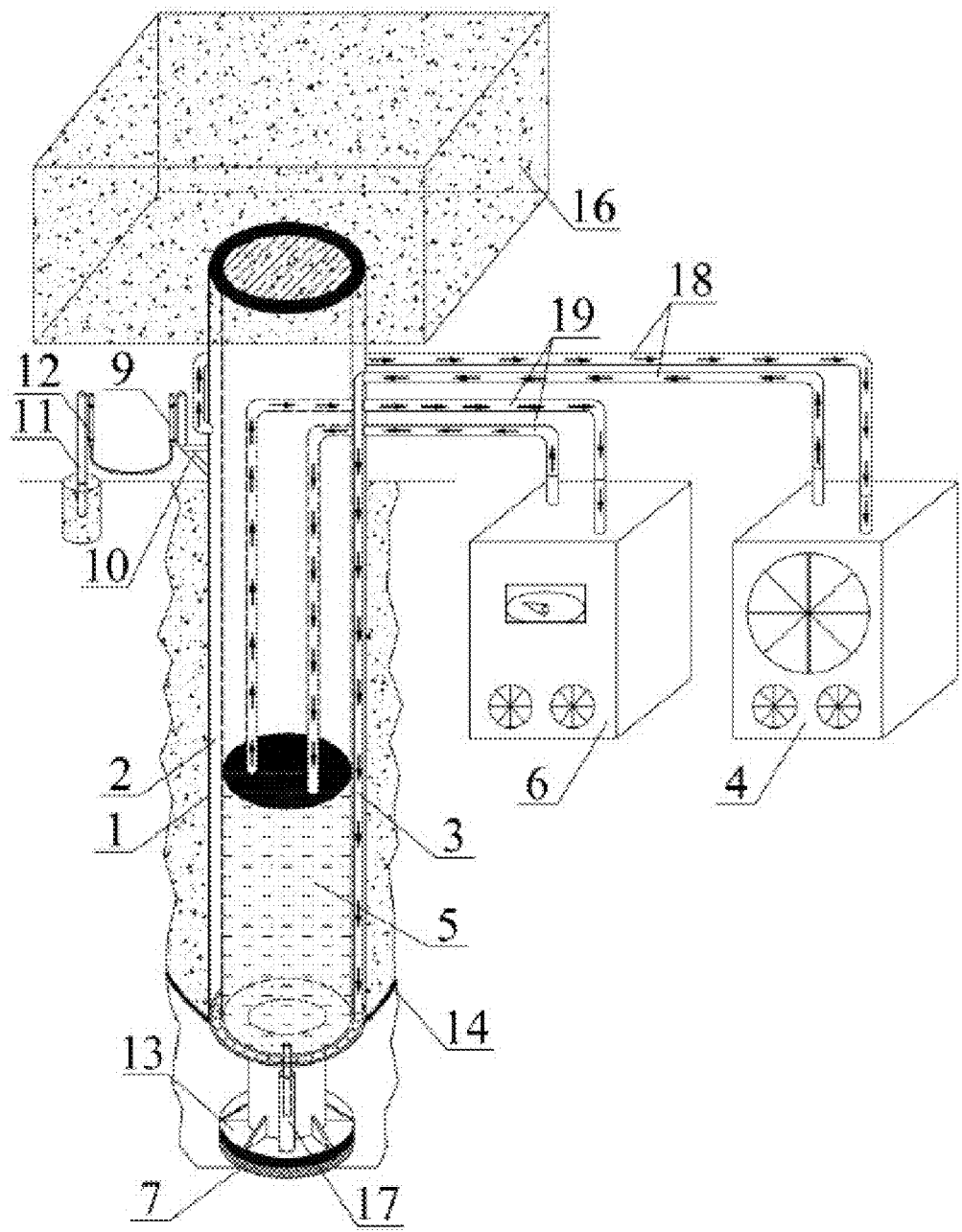
FIG. 1 is a schematic view of using the present invention for pile foundation monitoring of bored cast-in-place piles.
Figure 2:
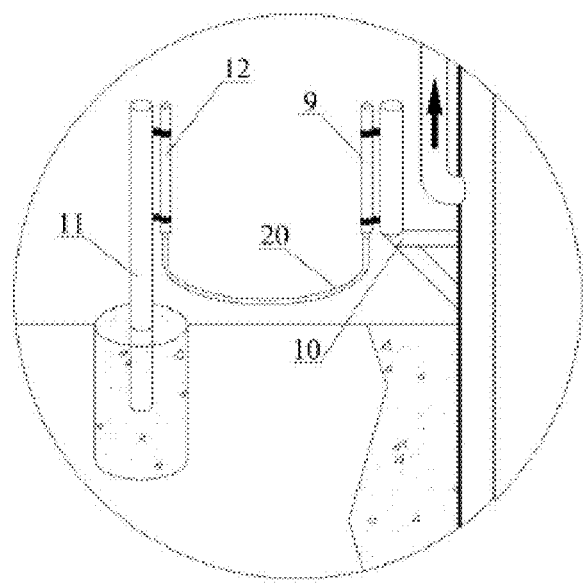
FIG. 2 is an exploded view of various parts of the pile top displacement monitoring assembly.
Figure 3:
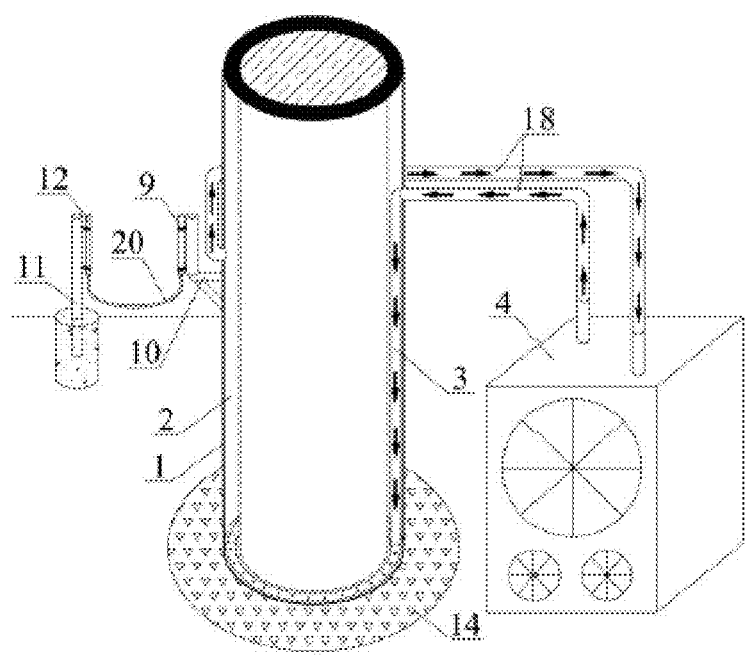
FIG. 3 is an exploded view of various parts of the pile body assembly in the present invention.
Figure 4:
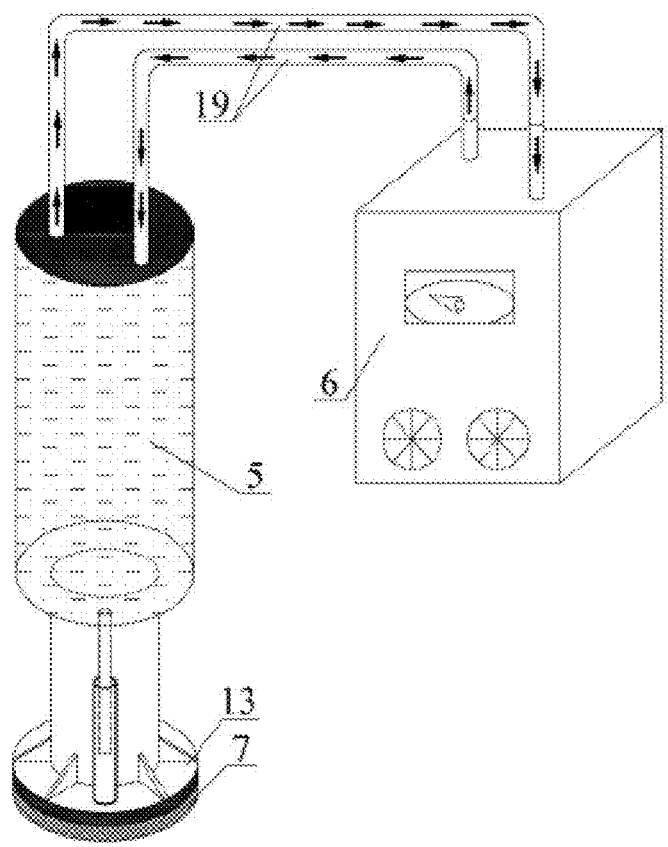
FIG. 4 is an exploded view of various parts of the pile body bottom load application assembly of the present invention.
Figure 5:
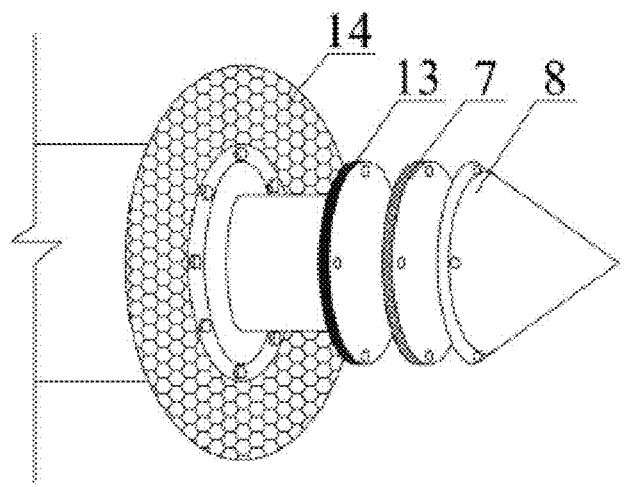
FIG. 5 is an exploded view of the ring and pointed boot at the bottom of the pile foundation.
Figure 6:
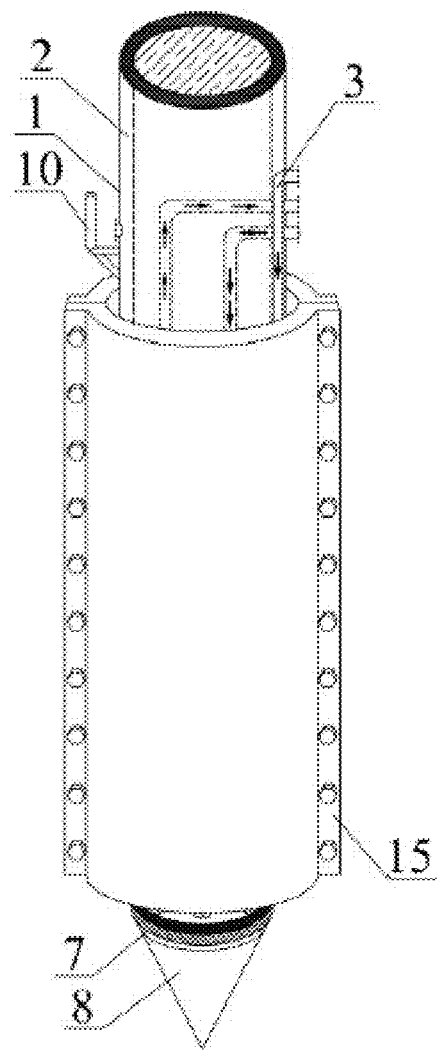
FIG. 6 is a schematic view of preparing a precast pile when the pile body is in the precast pile mold.

As shown in FIG. 1 to FIG. 6.

Embodiment 1: a pile foundation bearing performance testing device includes a pile body 1, a hydraulic jack 5 is provided inside a pile bottom of the pile body 1, and a piston lever head 13 of the hydraulic jack 5 is oriented downward, an earth pressure cell 7 is provided on the piston lever head 13 of the hydraulic jack 5, a pointed boot 8 is provided at a bottom of the earth pressure cell 7, and a ring 14 is provided at a lower portion of the pile body 1.

When the present invention is used, the hydraulic jack 5 is provided inside the pile bottom of the pile body 1, and a hydraulic machine 6 drives hydraulic fluid into the hydraulic jack 5 through a hydraulic oil pipeline 19 to eventually move the piston lever head 13, and during use, the piston lever head 13 is successively provided with the earth pressure cell 7 and the pointed boot 8 which can be fixed with bolts, wherein the pointed boot 8 is an inverted conical object made of steel; additionally, the ring 14 which is fixed with bolts is arranged at the bottom of the pile body 1. When the present invention is used for the cast-in-place pile bearing performance test, the pointed boot 8 should be removed and the ring 14 shall be installed at the bottom of the pile, and the ring 14 can prevent concrete from entering the space where the piston lever head 13 of the hydraulic jack 5 is located when concrete is poured between the pile body 1 and a drilled hole; when the present invention is used for the precast pile bearing performance test, the ring 14 should be removed from the bottom of the pile body 1, the piston lever head 13 of the hydraulic jack 5 should be pressed into the jack, and the pointed boot 8 should be bolted to the piston lever head 13 to press the precast pile into the permafrost layer. The pointed boot 8 is used in the precast pile bearing performance test, and the ring 14 is removed when the precast pile bearing performance test is conducted; the ring 14 is used in the cast-in-place pile bearing performance test, and the pointed boot 8 is removed in the cast-in-place pile bearing performance test; the earth pressure cell 7 is used to detect the pressure generated on the soil body when the piston lever head 13 of the hydraulic jack 5 is extended. The earth pressure cell 7 may be a double-membrane earth pressure cell, such as the earth pressure cell produced by Changsha Kingmach Measurement and Control Technology Co., Ltd., and the ring 14 is made of rubber.

An interlayer is disposed in a side wall of the pile body 1 to form a liquid-cooling chamber 2, a cold bath pipe 3 is provided inside the liquid-cooling chamber 2, a liquid outlet is configured on an outer wall of the pile body 1 located at an upper end of the liquid-cooling chamber 2, and the cold bath pipe 3 has a main body including a vertical steel pipe and a ring steel pipe with a hole and disposed at the bottom of the liquid-cooling chamber 2. The cold bath pipe 3 and the liquid outlet can be connected to a cold bath machine 4, and the cold bath machine 4 can be used to control the temperature of the antifreezing solution inside the cold bath machine 4 and change the temperature of the surrounding soil layer during or after the test.

The main body of the pile body 1 is a steel pipe, and a steel pipe with a diameter slightly smaller than that of the steel pipe of the pile body 1 is arranged inside it, steel rings are provided at the upper and lower ends of the two steel pipes, and the closed space formed by scaling and welding is the liquid-cooling chamber 2; the cold bath pipe 3 is arranged in the liquid-cooling chamber 2, and the cold bath pipe 3 has a main body including a vertical steel pipe and a ring steel pipe with a hole and disposed at the bottom of the liquid-cooling chamber 2; during the process of operation, the cold bath machine 4 is used to press a low-temperature resistant antifreezing solution into the cold bath pipe 3 via a cold bath delivery pipe 18 and the antifreezing solution enters the liquid-cooling chamber 2 via the cold bath pipe 3. A liquid outlet is arranged on an outer wall of the pile side located at the upper end of the liquid-cooling chamber 2 to allow the antifreezing solution to flow to the liquid outlet of the cold batch machine 4.

A water displacement gauge bracket 10 is provided at a side of a top of the pile body 1 for installation of a water displacement gauge tube No. 1 9, and in practical use, a reference point bracket 11 may be provided at a position which is spaced apart from the test pile by a certain distance and experiences no ground settlement during the test to install a water displacement gauge tube No. 2 12 thereon, and the water displace gauge tube No. 1 9 and the water displacement gauge tube No. 2 12 are connected through a low-temperature resistant water pipe 20. During the test process, the pile body 1 drives the water displacement gauge tube No. 1 9 to move up and down, and the vertical displacement of the pile body is recorded by recording the changes in the liquid level in the water displacement gauge tube No. 1 9, and the low-temperature resistant antifreezing solution can also be used in the tube body of the water displacement gauge.

A method for testing pile foundation bearing performance applied to a pile foundation bearing performance testing device, including a cast-in-place pile foundation bearing performance test in the following steps:

step A1, drilling a hole in a target test area to form a drilled hole, installing the ring 14 on a bottom end of the pile body 1, then placing the pile foundation bearing performance testing device into the drilled hole, pressurizing the hydraulic jack 5 with a hydraulic machine 6 so that the earth pressure cell 7 on the piston lever head 13 is in contact with a soil body at a bottom of the drilled hole, pouring concrete into a gap between the pile body 1 and the drilled hole, and curing the concrete;

step A2, pressurizing the hydraulic jack 5 with the hydraulic machine 6 so that the piston lever head 13 is accommodated into the hydraulic jack 5, at that time, applying a load to a top of the pile body is a pile foundation bearing performance test of a friction pile;

step A3, making the earth pressure cell 7 on the piston lever head 13 in full contact with the soil body and the earth pressure cell 7 show a pressure borne by a soil body at a pile tip, applying a load greater than the value of the pressure borne by the soil body at the pile tip shown by the earth pressure cell 7 to the top of the pile body is a service performance test of an end-bearing friction pile;

step A4, applying no load to the top of the pile body 1, and enabling the hydraulic jack 5 to drive the piston lever head 13 so that the earth pressure cell 7 or the pointed boot 8 is in full contact with the soil body is a service performance test of an uplift pile;

step A5, adjusting a pile side resistance and a pile tip resistance of the end-bearing friction pile, applying various overlying dead loads to the top of the pile body 1, and adjusting the load values applied to the pile body 1 and the soil body at the bottom of the drilled hole by the hydraulic jack 5 at the bottom of the pile body 1 to change the pile side resistance and the pile tip resistance as well as proportions thereof, where for the pile body 1, the difference between a load 16 applied to the top of the pile body 1 and the load applied by the hydraulic jack 5 is a value of the pile side resistance, and the value of the load applied by the hydraulic jack 5 to the soil body at the bottom of the drilled hole is a value of the pile tip resistance; and step A6, upon completion of the test, pulling the pile foundation bearing performance testing device attached with concrete out of the drilled hole using a crane, and removing the concrete on the surface of the pile body 1 by means of a concrete breaking hammer for next use of the pile foundation bearing performance testing device.

A displacement of the pile body 1 during the bearing performance test of the end-bearing friction pile is jointly measured by means of the water displacement gauge tube No. 1 9 installed on the top of the pile body 1 and the water displacement gauge tube No. 2 12 installed on the ground; and an electromagnetic displacement transducer 17 is additionally secured at the position of the piston lever head 13 of the hydraulic jack 5 for displacement monitoring, thus the difference between a pile top displacement and a pile bottom displacement is used to calculate a pile body displacement and a pile tip displacement of the end-bearing friction pile under different proportion conditions of the pile side resistance and the pile tip resistance.

During the test process, a cold bath machine 4 is used to adjust a temperature of an antifreezing solution entering the liquid-cooling chamber 2 of the pile body 1 to a target testing temperature, the pile foundation bearing performance is successively tested under different temperature conditions, and the cold bath machine 4 is adjusted to raise the temperature of the antifreezing solution entering the liquid-cooling chamber 2 of the pile body 1 to a positive temperature after completion of the test, so as to thaw frozen soil around the pile body, and the hydraulic jack 5 is pressurized by means of the hydraulic machine 6 to make the piston lever head 13 pressurize the soil body at the bottom of the drilled hole, so that the pile body and the thawed soil are released from the frozen state.

Embodiment 2: On the basis of Embodiment 1, a method for testing pile foundation bearing performance applied to a pile foundation bearing performance testing device: including testing the precast pile foundation bearing performance in the following steps:

step B1: accommodating the piston lever head 13 into the hydraulic jack 5, installing the pointed boot 8 onto the outside of the earth pressure cell 7 of the piston lever head 13, and removing the ring 14 if it is installed at the bottom of the pile body 1;

step B2, placing the pile foundation bearing performance testing device into the precast pile mold 15, pouring concrete in the gap between the pile body 1 and the precast pile mold 15, and removing the precast pile mold after curing until the concrete reaches strength to form a precast pile;

step B3, using pile pressing equipment to press the precast pile into a soil layer;

step B4, pressurizing the hydraulic jack 5 with the hydraulic machine 6 so that the piston lever head 13 is accommodated into the hydraulic jack 5, at that time, applying a load to a top of the pile body is a pile foundation bearing performance test of a friction pile;

step B5, making the pointed boot 8 on the piston lever head 13 in full contact with the soil body and the earth pressure cell 7 show a pressure borne by a soil body at a pile tip, applying a load greater than the value of the pressure borne by the soil body at the pile tip shown by the earth pressure cell 7 to the top of the pile body is a service performance test of an end-bearing friction pile;

step B6, applying no load to the top of the pile body 1, and enabling the hydraulic jack 5 to drive the piston lever head 13 so that the pointed boot 8 is in full contact with the soil body is a service performance test of an uplift pile;

step B7, adjusting a pile side resistance and a pile tip resistance of the end-bearing friction pile, applying various overlying dead loads to the top of the pile body 1, and adjusting the load values applied to the pile body 1 and the soil body of the soil layer by the hydraulic jack 5 at the bottom of the pile body 1 to change the pile side resistance and the pile tip resistance as well as proportions thereof, where for the pile body 1, the difference between a load 16 applied to the top of the pile body 1 and the load applied by the hydraulic jack 5 is a value of the pile side resistance, and the value of the load applied by the hydraulic jack 5 to the soil body of the soil layer is a value of the pile tip resistance; and step B8, upon completion of the test, pulling the pile foundation bearing performance testing device attached with concrete out of the soil layer using a crane, and removing the concrete on the surface of the pile body 1 by means of a concrete breaking hammer for next use of the pile foundation bearing performance testing device.

A displacement of the pile body 1 during the bearing performance test of the end-bearing friction pile is jointly measured by means of the water displacement gauge tube No. 1 9 installed on the top of the pile body 1 and the water displacement gauge tube No. 2 12 installed on the ground; and an electromagnetic displacement transducer 17 is additionally secured at the position of the piston lever head 13 of the hydraulic jack 5 for displacement monitoring, thus the difference between a pile top displacement and a pile bottom displacement is used to calculate a pile body displacement and a pile tip displacement of the end-bearing friction pile under different proportion conditions of the pile side resistance and the pile tip resistance.

During the test process, a cold bath machine 4 is used to adjust a temperature of an antifreezing solution entering the liquid-cooling chamber 2 of the pile body 1 to a target testing temperature, the pile foundation bearing performance is successively tested under different temperature conditions, and the cold bath machine 4 is adjusted to raise the temperature of the antifreezing solution entering the liquid-cooling chamber 2 of the pile body 1 to a positive temperature after completion of the test, so as to thaw frozen soil around the pile body, and the hydraulic jack 5 is pressurized by means of the hydraulic machine 6 to make the piston lever head 13 pressurize the soil body at the bottom of the drilled hole, so that the pile body and the thawing soil are released from the frozen state.

Principle of operation: the method of operation in the cast-in-place pile foundation bearing performance test is as follows: step 1, drilling a hole in a target test area to form a drilled hole; step 2, installing the ring 14 in the present invention on the bottom end of the pile body 1, then placing the present invention into the drilled hole, and pressurizing the hydraulic jack 5 with a hydraulic machine 6 so that the earth pressure cell 7 on the piston lever head 13 is in contact with a soil body at a bottom of the drilled hole; step 3, pouring concrete in the gap between the pile body 1 and the drilled hole, and curing the concrete; step 4, adjusting the cold bath machine 4 to successively control a temperature of the antifreezing solution entering the liquid-cooling chamber 2 of the pile body 1 to a target testing temperature, and successively testing the pile foundation bearing performance under different temperature conditions; step 5, adjusting the cold bath machine 4 to raise the temperature of the antifreezing solution entering the liquid-cooling chamber 2 of the pile body 1 to a positive temperature, so as to thaw frozen soil around the pile body, and pressurizing the hydraulic jack 5 by means of the hydraulic machine 6 to make the piston lever head 13 pressurize the soil body at the bottom of the drilled hole, so that the pile body and the thawed soil are released from the frozen state, and subsequently, pulling the present invention attached with concrete out of the drilled hole using a crane; step 6: removing the concrete on the surface of the pile body 1 in the present invention by means of a concrete breaking hammer for next use of the pile foundation bearing performance testing device.

The method of operation in the precast pile foundation bearing performance test is as follows: step 1, accommodating the piston lever head 13 on the hydraulic jack 5 in the present invention into the hydraulic jack 5, installing the pointed boot 8 onto the outside of the earth pressure cell 7 of the piston lever head 13, and removing the ring 14 if it is installed at the bottom of the pile body 1; step 2, placing the present invention into the precast pile mold 15, pouring concrete into the gap between the pile body 1 of the present invention and the precast pile mold 15, and removing the mold after curing until the concrete reaches strength to form a precast pile; step 3, using pile pressing equipment to press the precast pile into the permafrost layer, and pressurizing the hydraulic jack 5 by means of the hydraulic machine 6 to make the pointed boot on the piston lever head 13 in full contact with the soil body; step 4, adjusting the cold bath machine 4 to successively control a temperature of the antifreezing solution entering the liquid-cooling chamber 2 of the pile body 1 to a target testing temperature, and successively testing the pile foundation bearing performance under different temperature conditions; step 5, adjusting the cold bath machine 4 to raise the temperature of the antifreezing solution entering the liquid-cooling chamber 2 of the pile body 1 to a positive temperature, so as to thaw frozen soil around the pile body, and pressurizing the hydraulic jack 5 by means of the hydraulic machine 6 to make the piston lever head 13 pressurize the soil body, so that the pile body and the thawing soil are released from the frozen state, and subsequently, pulling the present invention attached with concrete out of the soil layer using a crane; step 6: removing the concrete on the surface of the pile body 1 in the present invention by means of a concrete breaking hammer for next use of the pile foundation bearing performance testing device.

The method of switching between the service performance tests of end-bearing friction piles, friction piles, and uplift piles is as follows: pressurizing the hydraulic jack 5 with the hydraulic machine 6 so that the piston lever head 13 is accommodated into the hydraulic jack 5, at that time, applying a load to a top of the pile body is a pile foundation bearing performance test of a friction pile; making the earth pressure cell 7 or the pointed boot 8 on the piston lever head 13 in full contact with the soil body and the earth pressure cell 7 show a pressure borne by a soil body at a pile tip, applying a load greater than the value of the pressure borne by the soil body at the pile tip shown by the earth pressure cell 7 to the top of the pile body is a service performance test of an end-bearing friction pile; and applying no load to the top of the pile body 1, and enabling the hydraulic jack 5 to drive the piston lever head 13 so that the earth pressure cell 7 or the pointed boot 8 is in full contact with the soil body is a service performance test of an uplift pile.

The method of operation for adjusting the pile side resistance and pile tip resistance of an end-bearing friction pile: applying various overlying dead loads to the top of the pile body 1 in the present invention, and adjusting the load values applied to the pile body 1 and the soil body at the bottom of the drilled hole by the hydraulic jack 5 at the bottom of the pile body 1 to change the pile side resistance and the pile tip resistance as well as proportions thereof, where for the pile body 1, the difference between a load 16 applied to the top of the pile body 1 and the load applied by the hydraulic jack 5 is a value of the pile side resistance, and the value of the load applied by the hydraulic jack 5 to the soil body at the bottom of the drilled hole is a value of the pile tip resistance; at the context of the end-bearing friction pile bearing performance test, measuring a displacement of the pile body 1 during the bearing performance test of the end-bearing friction pile jointly by means of the water displacement gauge tube No. 1 9 installed on the top of the pile body 1 and the water displacement gauge tube No. 2 12 installed on the ground; and additionally, securing an electromagnetic displacement transducer 17 at the position of the piston lever head 13 of the hydraulic jack 5 for displacement monitoring, thus the difference between a pile top displacement and a pile bottom displacement is used to calculate a pile body displacement and a pile tip displacement of the end-bearing friction pile under different proportion conditions of the pile side resistance and the pile tip resistance.

The main body of the present invention is a pile body provided with a hydraulic jack at the bottom, and in the end-bearing friction pile test, the pile foundation service performance test is conducted under different conditions of the pile side resistance and the pile tip resistance by applying the upper dead load to the top of the pile body and applying the load at the bottom of the pile by means of the hydraulic jack; by enabling the hydraulic jack at the bottom of the present invention to drive the piston lever head to detach from the contact with the soil at the pile tip, the end-bearing friction pile can become the friction pile, and the present invention can carry out the pile foundation bearing performance test of a pressure-bearing friction pile; by enabling the hydraulic jack at the bottom of the present invention to drive the piston lever head to contact the soil at the pile tip, so that the pile body undergoes upward movement relative to the soil around the pile, the uplift pile service performance test can be conducted; the temperature of soil around the pile is controlled by enabling the cold bath machine to inject an antifreezing solution into the liquid-cooling chamber inside the pile body and circulate it, and combined with different methods for applying loads to the pile foundation, the pile foundation service performance tests of pressure-bearing end-bearing friction piles, pressure-bearing friction piles and uplift piles can be realized at different ground temperatures. Compared with the previous cast-in-place test piles, the present invention can test the pile foundation bearing performance at different ground temperatures; the present invention can study the deterioration in the pile foundation service performance caused by changes in the proportion of the pile side resistance and the pile tip resistance due to fluctuations in ground temperatures; the present invention can artificially change the proportion of the pile side resistance and the pile tip resistance by arranging the hydraulic jack at the bottom of the pile foundation and applying a dead load on the top of the pile with concrete blocks and can be used to test the pile foundation service performance of pressure-bearing end-bearing friction piles, pressure-bearing friction piles, uplift piles, etc.; concrete is poured onto the surface of the pile body in the present invention to form a precast pile, and the precast pile is driven into permafrost to realize the load service performance test of the precast pile in the permafrost area; the present invention is placed in a drilled hole and concrete is poured around a pile to realize the pile foundation service performance test of a bored cast-in-place pile; in addition to being used in the permafrost areas, the present invention can also be used in non-permafrost areas, with the same application prospects as those in the permafrost areas; the present invention has the advantage of a low level of difficulty in reuse difficulty, and the permafrost around the pile can thaw by enabling the cold bath machine to inject a high-temperature antifreezing solution into the pile body, and after the freezing force between the pile and permafrost disappears, a crane can be used to remove the present invention from the pile hole for reuse.

The above are only preferred embodiments of the present invention.

What is claimed is:

1. A method for testing pile foundation bearing performance, comprising conducting a cast-in-place pile foundation bearing performance test by means of a pile foundation bearing performance testing device, wherein the pile foundation bearing performance testing device comprises a pile body, a hydraulic jack is provided inside a pile bottom of the pile body, and a piston lever head of the hydraulic jack is oriented downward, an earth pressure cell is provided on the piston lever head of the hydraulic jack, an interlayer is disposed inside a side wall of the pile body to form a liquid-cooling chamber, a cold bath pipe is provided inside the liquid-cooling chamber, a liquid outlet is configured on an outer wall of the pile body located at an upper end of the liquid-cooling chamber, the cold bath pipe has a main body comprising a vertical steel pipe and a ring steel pipe with a hole and disposed at the bottom of the liquid-cooling chamber, a water displacement gauge bracket is provided at a side of a top of the pile body for installation of a water displacement gauge tube No. 1, and, a reference point bracket is provided at a position which is spaced apart from the test pile by a certain distance and experiences no ground settlement during the test to install a water displacement gauge tube No. 2 thereon, and the water displacement gauge tube No. 1 and the water displacement gauge tube No. 2 are connected through a low-temperature resistant water pipe, the cast-in-place pile foundation bearing performance test comprises the following steps:

step A1, drilling a hole in a target test area to form a drilled hole, installing the ring on a bottom end of the pile body, then placing the pile foundation bearing performance testing device into the drilled hole, pressurizing the hydraulic jack with a hydraulic machine so that the earth pressure cell on the piston lever head is in contact with a soil body at a bottom of the drilled hole, pouring concrete into a gap between the pile body and the drilled hole, and curing the concrete;

step A2, pressurizing the hydraulic jack with the hydraulic machine so that the piston lever head is accommodated into the hydraulic jack, at that time, applying a load to a top of the pile body, to perform a pile foundation bearing performance test of a friction pile;

step A3, making the earth pressure cell on the piston lever head in full contact with the soil body and the earth pressure cell show a pressure borne by a soil body at a pile tip, applying a load greater than a value of the pressure borne by the soil body at the pile tip shown by the earth pressure cell to the top of the pile body, to perform a service performance test of an end-bearing friction pile;

step A4, applying no load to the top of the pile body, and enabling the hydraulic jack to drive the piston lever head so that the earth pressure cell is in full contact with the soil body, to perform a service performance test of an uplift pile; and step A5, adjusting a pile side resistance and a pile tip resistance of the end-bearing friction pile, applying various overlying dead loads to the top of the pile body, and adjusting the load values applied to the pile body and the soil body at the bottom of the drilled hole by the hydraulic jack at the bottom of the pile body to change the pile side resistance and the pile tip resistance as well as proportions thereof, where for the pile body, a difference between a load applied to the top of the pile body and the load applied by the hydraulic jack is a value of the pile side resistance, and the value of the load applied by the hydraulic jack to the soil body at the bottom of the drilled hole is a value of the pile tip resistance.

2. The method for testing pile foundation bearing performance according to claim 1, a displacement of the pile body during the bearing performance test of the end-bearing friction pile is jointly measured by means of the water displacement gauge tube No. 1 installed on the top of the pile body and the water displacement gauge tube No. 2 installed on the ground; and an electromagnetic displacement transducer is additionally secured at the position of the piston lever head of the hydraulic jack for displacement monitoring, thus the difference between a pile top displacement and a pile bottom displacement is used to calculate a pile body displacement and a pile tip displacement of the end-bearing friction pile under different proportion conditions of the pile side resistance and the pile tip resistance.

3. The method for testing pile foundation bearing performance according to claim 2, during a test process, a cold bath machine is used to adjust a temperature of antifreezing solution entering the liquid-cooling chamber of the pile body to a target testing temperature, the pile foundation bearing performance is successively tested under different temperature conditions, and the cold bath machine is adjusted to raise the temperature of the antifreezing solution entering the liquid-cooling chamber of the pile body to a positive temperature after completion of the test, so as to thaw frozen soil around the pile body, and the hydraulic jack is pressurized by means of the hydraulic machine to make the piston lever head pressurize the soil body at the bottom of the drilled hole, so that the pile body and the thawed soil are released from a frozen state.

4. The method for testing pile foundation bearing performance according to claim 1, comprising a precast pile foundation bearing performance test with steps shown as follows:

step B1: accommodating the piston lever head into the hydraulic jack, and installing a pointed boot onto an outside of the earth pressure cell of the piston lever head;

step B2, placing the pile foundation bearing performance testing device into a precast pile mold, pouring concrete in the gap between the pile body and the precast pile mold, and removing the precast pile mold after curing until the concrete reaches strength to form a precast pile;

step B3, using pile pressing equipment to press the precast pile into a soil layer;

step B4, pressurizing the hydraulic jack with the hydraulic machine so that the piston lever head is accommodated into the hydraulic jack, at that time, applying a load to a top of the pile body, to perform the pile foundation bearing performance test of a friction pile;

step B5, making the pointed boot on the piston lever head in full contact with the soil body and the earth pressure cell show a pressure borne by a soil body at a pile tip, applying a load greater than the value of the pressure borne by the soil body at the pile tip shown by the earth pressure cell to the top of the pile body, to perform the service performance test of an end-bearing friction pile;

step B6, applying no load to the top of the pile body, and enabling the hydraulic jack to drive the piston lever head so that the pointed boot is in full contact with the soil body, to perform the service performance test of an uplift pile; and step B7, adjusting a pile side resistance and a pile tip resistance of the end-bearing friction pile, applying various overlying dead loads to the top of the pile body, and adjusting the load values applied to the pile body and the soil body of the soil layer by the hydraulic jack at the bottom of the pile body to change the pile side resistance and the pile tip resistance as well as proportions thereof, where for the pile body, a difference between a load applied to the top of the pile body and the load applied by the hydraulic jack is a value of the pile side resistance, and the value of the load applied by the hydraulic jack to the soil body of the soil layer is a value of the pile tip resistance.

5. The method for testing pile foundation bearing performance according to claim 4, a displacement of the pile body during the bearing performance test of the end-bearing friction pile is jointly measured by means of the water displacement gauge tube No. 1 installed on the top of the pile body and the water displacement gauge tube No. 2 installed on the ground; and an electromagnetic displacement transducer is additionally secured at the position of the piston lever head of the hydraulic jack for displacement monitoring, thus the difference between a pile top displacement and a pile bottom displacement is used to calculate a pile body displacement and a pile tip displacement of the end-bearing friction pile under different proportion conditions of the pile side resistance and the pile tip resistance.

6. The method for testing pile foundation bearing performance according to claim 5, during a test process, a cold bath machine is used to adjust a temperature of antifreezing solution entering the liquid-cooling chamber of the pile body to a target testing temperature, the pile foundation bearing performance is successively tested under different temperature conditions, and the cold bath machine is adjusted to raise the temperature of the antifreezing solution entering the liquid-cooling chamber of the pile body to a positive temperature after completion of the test, so as to thaw frozen soil around the pile body, and the hydraulic jack is pressurized by means of the hydraulic machine to make the piston lever head pressurize the soil body of the soil layer, so that the pile body and the thawed soil are released from a frozen state.

\* \* \* \* \*